(12) United States Patent
McNeary

(10) Patent No.: US 8,206,757 B2
(45) Date of Patent: Jun. 26, 2012

(54) COMPOSITION OF ASHWAGANDHA AND INDIAN GOOSEBERRY

(75) Inventor: Peter McNeary, Brattleboro, VT (US)

(73) Assignees: Nutragenesis, LLC, Brattleboro, VT (US); Natreon, Inc., New Brunswick, NJ (US)

( * ) Notice: Subject to any disclaimer, the term of this patent is extended or adjusted under 35 U.S.C. 154(b) by 0 days.

(21) Appl. No.: 12/604,092

(22) Filed: Oct. 22, 2009

(65) Prior Publication Data

US 2010/0098785 A1 Apr. 22, 2010

Related U.S. Application Data

(60) Provisional application No. 61/107,573, filed on Oct. 22, 2008.

(51) Int. Cl.
*A61K 36/00* (2006.01)

(52) U.S. Cl. .................................... 424/725

(58) Field of Classification Search .................. None
See application file for complete search history.

(56) References Cited

U.S. PATENT DOCUMENTS

| | | | |
|---|---|---|---|
| 6,235,721 B1 | 5/2001 | Ghosal | |
| 6,362,167 B1 | 3/2002 | Ghosal | |
| 7,001,619 B2 | 2/2006 | Johri et al. | |
| 2006/0147561 A1* | 7/2006 | Pushpangadan et al. | 424/734 |
| 2006/0172021 A1* | 8/2006 | Moffett | 424/725 |

FOREIGN PATENT DOCUMENTS

| | | | |
|---|---|---|---|
| FR | 2902656 A1 | * | 12/2007 |
| IN | 200500654 I | * | 3/2006 |
| JP | 2003300824 A | * | 10/2003 |

OTHER PUBLICATIONS

Berenbaum, Synergy, additivism and antagonism in immunosuppression, Clin. Esp. Immunol (1977) 28, 1-18.*
Parle et al, Traditional medicinal formulation, Chyawanprash, Indian Journal of Traditional Knowledge vol. 5 (4), 2006, pp. 484-488.*
"EnzChek Gelatinase/Collagenase Assay Kit." Molecular Probes Product Information, Revised: Mar. 22, 2001.
"Novel Fluorometric Assay for Hydroxyl Radical Prevention Capacity Using Fluorescein as the Probe." Journal of Agricultural and Food Chemistry, 2002, vol. 50, pp. 2772-2777.
"Development and Validation of an Improved Oxygen Radical Absorbance Capacity Assay Using Fluorescein as the Fluorescent Probe." Journal of Agricultural and Food Chemistry, 2001, vol. 49, pp. 4619-4626.
"Inhibition of Hyaluronidase Adapted from: Enzymatic Assay of Hyaluronidase," by A. Dorfman. Methods in Enzymology, vol. I, pp. 166-173 (1955).
Declaration of Bruce Abedon Regarding Chyawanprash dated Mar. 30, 2011.
Office Action dated Nov. 15, 2011 in related U.S. Appl. No. 12/710,843, filed Feb. 23, 2010, in the name of Peter S. McNeary.
Hanif et al., "Antioxidant Factor of Amla Fruit," Pakistan Journal of Scientific Research (1966), 18(1), 61-3.
Khopde et al., "Characterizing the Antioxidant Activity of Amla (*Phyllanthus emblica*) Extract," Current Science (2001) vol. 81, No. 2, pp. 185-190.
Banerjee et al., "Preparation, Evaluation and Hair Growth Stimulating Activity of Herbal Hair Oil," Journal of Chemical and Pharmaceutical Research (2009) vol. 1, No. 1, pp. 261-267.
Edeas, "Citrus Bioflavonoids," Phytotherapie, Oct. 2007, vol. 5, No. 4, pp. 210-211.

* cited by examiner

*Primary Examiner* — Qiuwen Mi
(74) *Attorney, Agent, or Firm* — Downs Rachlin Martin PLLC

(57) ABSTRACT

A therapeutic composition comprising extracts of the plant species ashwagandha (*Withania somnifera*) and Indian gooseberry (*Phyllanthus emblica*). A composition of ashwagandha and Indian gooseberry may: (1) lower cortisol and increase DHEA, (2) prevents free radical-induced photoaging, (3) inhibit collagenase activity in vitro, (4) inhibit hyaluronidase activity in vitro, (5) display superior cascading antioxidant activity, (6) reduce C-reactive protein, (7) enhance mood.

12 Claims, 1 Drawing Sheet

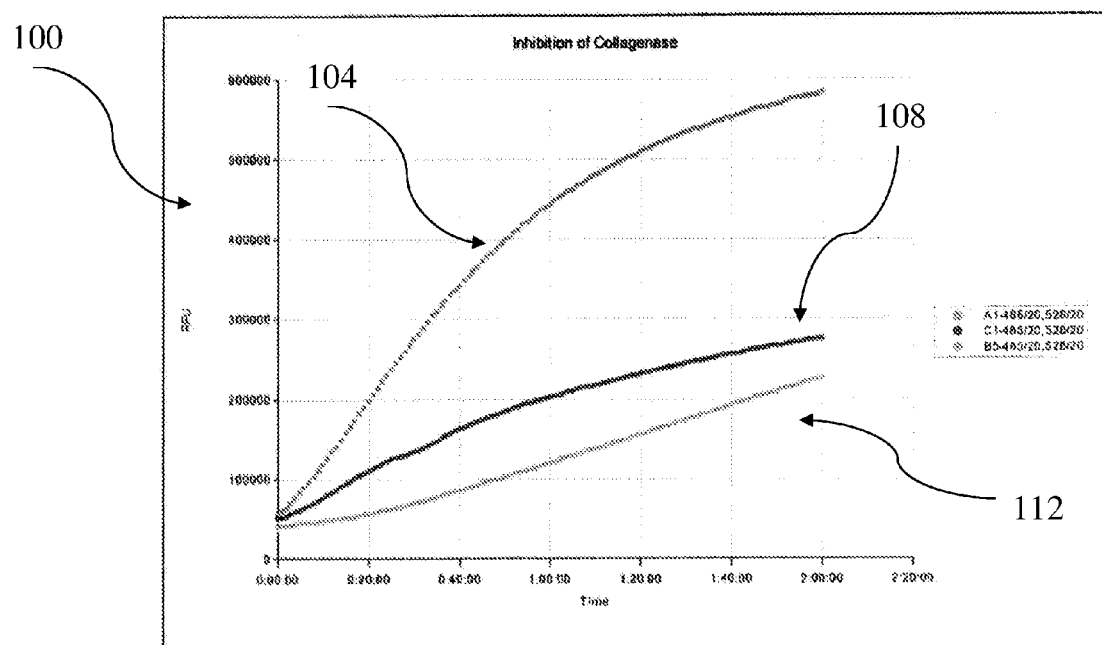

COMPOSITION OF ASHWAGANDHA AND INDIAN GOOSEBERRY

RELATED APPLICATION DATA

This application claims the benefit of priority of U.S. Provisional Patent Application Ser. No. 61/107,573, filed Oct. 22, 2008, and titled "Composition of Ashwagandha and Indian Gooseberry," which is incorporated by reference herein in its entirety.

FIELD OF THE INVENTION

The present invention generally relates to the field of botanical drugs or dietary supplements related to skin-care and/or emotional well-being. In particular, the present invention is directed to an improved health composition of ashwagandha and Indian gooseberry.

BACKGROUND

Multiple factors cause accelerated aging of the skin. Prolonged periods of stress result in hormonal changes and restricted nutrient flow to the skin which can lead to a person physically aging right before our eyes. Environmental stressors like UV light and chemical pollutants, as well as regular metabolic activity, create destructive enzymes and free radicals in the body. These break down skin-strengthening collagen and skin-hydrating hyaluronic acid, leading to the fine lines, wrinkles, and dry, sagging skin associated with an aged appearance.

The mind-skin connection is strong. So strong in fact that there is a burgeoning field in dermatology referred to as "psychodermatology" that addresses how an individual's emotional state affects skin health and appearance. Irritability, a negative outlook and other feelings resulting from stress can contribute to aging of the skin through physiological processes similar to how stress affects the rest of the body.

Chronic, emotional stress is a major contributor to accelerated aging, having widespread ramifications throughout the body due in large part to hormonal changes that occur in response to the stress. When the body is under chronic stress, cortisol levels in the blood rise and dehydroepiandrosterone (DHEA) levels fall. Associated with these hormonal changes is a reduction in feelings of well-being such as increased anxiety, irritability, and insomnia. The combination of hormonal and emotional changes puts strain on an assortment of body tissues, including the skin, leading to signs of premature aging.

Current natural products have limited effectiveness against the many causes of premature skin aging and therefore generally do not substantially improve the skin and the emotional state of the person taking the product.

SUMMARY OF THE DISCLOSURE

One aspect of the present invention is a therapeutic composition for use in the reduction of premature skin aging in a human subject comprising a skin age reducing synergistically effective combination of an extract of *Phyllanthus emblica* and an extract of *Withania somnifera* wherein the *Phyllanthus emblica* and the *Withania somnifera* are present in the composition in a weight ratio of about 1:7 *Phyllanthus emblica* to *Withania somnifera* to a weight ratio of about 7:1 *Phyllanthus emblica* to *Withania somnifera*.

Another aspect of the present invention is a therapeutic composition for use in the reduction of premature skin aging comprising an age reducing synergistically effective combination of an extract of *Phyllanthus emblica* and an extract of *Withania somnifera* wherein the composition includes about 60 wt. % *Withania somnifera* to about 65 wt. % *Withania somnifera* and about 35 wt. % *Phyllanthus emblica* to about 40 wt. % *Phyllanthus emblica*.

Yet another aspect of the present invention is a method of preventing photoaging comprising administering to a human a therapeutic composition comprising a synergistically effective combination of extracts of *Phyllanthus emblica* and *Withania somnifera*.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 1 is a graph of the number of relative fluorescence units over time for three different inhibition data sets.

DETAILED DESCRIPTION

An improved health composition is provided that includes a combination of ashwagandha (*Withania somnifera*) and Indian gooseberry (*Phyllanthus emblica*). In one example, the improved health composition may be capable of being ingested by a human. In such an example, one or more of the health benefits discussed herein attributable to an improved health composition having ashwagandha and Indian gooseberry may be attainable through the ingestion of the composition by a human.

Capable of being ingested by a human may include, but is not limited to, the inclusion of an improved health composition of the present disclosure in a beverage (e.g., hot, cold, etc.). Ingestion of an improved health composition of the present disclosure may also be facilitated, for example, by including a combination of ashwagandha and Indian gooseberry as described herein in a nutritional product (e.g., a soup, a vitamin enriched granola bar, a nutritional bar, whole grain bread), a dietary supplement, a food product (e.g., hot, cold, etc.), a confectionary, an oil, a meal replacement, a cereal, a baked good, a candy, a gum, a lozenge, and any combinations thereof.

Ashwagandha is a naturally occurring substance from the *Withania somnifera* plant. In one example, it is utilized in a composition as described herein in the form of an extract. Various methods for extracting botanical extracts are known to those of ordinary skill In one example, Ashwagandha as used in one or more exemplary composition as described herein includes an ashwagandha extract prepared according to one or more methodologies set forth in U.S. Pat. No. 6,713,092 to Ghosal, entitled "*Withania Somnifera* Composition, Method For Obtaining Same And Pharmaceutical, Nutritional And Personal Care Formulations Thereof", the descriptions of which are is incorporated herein by reference in their entirety. In another example, an improved health composition includes Ashwagandha extract according to one or more of the examples set forth in U.S. Pat. No. 6,713,092 to Ghosal, entitled "*Withania Somnifera* Composition", the descriptions of which are incorporated herein by reference in their entirety. In another example, Ashwagandha as used in one or more exemplary compositions as described herein is an ashwagandha extract prepared according to one or more methodologies set forth in U.S. Pat. No. 6,153,198 to Ghosal, entitled "*Withania Somnifera* Composition", the descriptions of which are is incorporated herein by reference in their entirety.

Indian gooseberry is a naturally occurring substance from the *Phyllanthus emblica* plant. In one example, it is utilized in a composition as described herein in the form of an extract. Various methods for extracting botanical extracts are known to those of ordinary skill In one example, an improved health composition includes Indian gooseberry extract according to one or more of the examples set forth in U.S. Pat. No. 6,362,167 to Ghosal, entitled "Method Of Blocking Free Radical Processes Which Result In Mediated Pathology Without Deleterious Pro-oxidant Side Reactions", the descriptions of which are is incorporated herein by reference in their entirety. In another example, as used in one or more exemplary composition as described herein includes an Indian gooseberry extract prepared according to one or more methodologies set forth in U.S. Pat. No. 6,362,167 to Ghosal, entitled "Method Of Blocking Free Radical Processes Which Result In Mediated Pathology Without Deleterious Pro-oxidant Side Reactions", the descriptions of which are is incorporated herein by reference in their entirety. In another example, an improved health composition includes Indian gooseberry extract according to one or more of the examples set forth in U.S. Pat. No. 6,290,996 to Ghosal, entitled "Method of Inhibiting Blood Platelet Aggregation", the descriptions of which are is incorporated herein by reference in their entirety. In another example, as used in one or more exemplary composition as described herein is an Indian gooseberry extract prepared according to one or more methodologies set forth in U.S. Pat. No. 6,290,996 to Ghosal, entitled "Method of Inhibiting Blood Platelet Aggregation", the descriptions of which are is incorporated herein by reference in their entirety. In another example, Indian gooseberry as used in one or more exemplary composition as described herein includes an Indian gooseberry extract prepared according to one or more methodologies set forth in U.S. Pat. No. 6,124,268 to Ghosal, entitled "Natural Antioxidant Compositions, Method For Obtaining Same And Cosmetic, Pharmaceutical, And Nutritional Formulations Thereof", the descriptions of which are is incorporated herein by reference in their entirety. In one example, an improved health composition includes Indian gooseberry extract according to one or more of the examples set forth in U.S. Pat. No. 6,124,268 to Ghosal, entitled "Natural Antioxidant Compositions, Method For Obtaining Same And Cosmetic, Pharmaceutical, And Nutritional Formulations Thereof", the descriptions of which are is incorporated herein by reference in their entirety.

In another example, an improved health composition includes about 60 wt. % ashwagandha to about 65 wt. % ashwagandha and about 35 wt. % Indian gooseberry to about 40 wt. % Indian gooseberry. This composition achieves one or more of the benefits disclosed herein.

In another example, an improved health composition includes ashwagandha and Indian gooseberry in a weigh to weight ratio of about 1:7 to about 7:1. This composition achieves one or more of the benefits disclosed herein.

In another example, an improved health composition includes ashwagandha and Indian gooseberry in a weight to weight ratio of about 6:2 to about 2:6. This composition achieves one or more of the benefits disclosed herein.

In another example, an improved health composition includes ashwagandha and Indian gooseberry in a weight to weight ratio of about 6:2 to about 2:2. This composition achieves one or more of the benefits disclosed herein.

In another example, an improved health composition includes ashwagandha and Indian gooseberry in a weight to weight ratio of about 6:2 to about 3:5. This composition achieves one or more of the benefits disclosed herein.

In another example, an improved health composition includes ashwagandha and Indian gooseberry in a weight to weight ratio of about 6:2 to about 4:4. This composition achieves one or more of the benefits disclosed herein.

In another example, an improved health composition includes 60 wt. % ashwagandha to 65 wt. % ashwagandha and 35 wt. % Indian gooseberry to 40 wt. % Indian gooseberry. This composition achieves one or more of the benefits disclosed herein.

In another example, an improved health composition includes ashwagandha and Indian gooseberry in a weigh to weight ratio of 1:7 to 7:1. This composition achieves one or more of the benefits disclosed herein.

In another example, an improved health composition includes ashwagandha and Indian gooseberry in a weight to weight ratio of 6:2 to 2:6. This composition achieves one or more of the benefits disclosed herein.

In another example, an improved health composition includes ashwagandha and Indian gooseberry in a weight to weight ratio of 6:2 to 3:5. This composition achieves one or more of the benefits disclosed herein.

In another example, an improved health composition includes ashwagandha and Indian gooseberry in a weight to weight ratio of 6:2 to 2:2. This composition achieves one or more of the benefits disclosed herein.

In another example, an improved health composition includes ashwagandha and Indian gooseberry in a weight to weight ratio of 6:2 to 4:4. This composition achieves one or more of the benefits disclosed herein.

Aging of the skin is caused by a variety of factors. Intrinsic factors include secretion of stress hormones and toxic by-products of normal chemical reactions that take place within cells of the body. When hormones are released in response to stress, delivery of blood to dermal tissues is reduced. Normally, blood carries oxygen, water, and other vital nutrients to the body's surface and removes wastes. If this flow is impaired, the skin can weaken, become dry, and display uneven skintones. An improved health composition of ashwagandha, *Withania somnifera*, and Indian gooseberry, *Phyllanthus emblica*, according to the current disclosure may boost resistance to premature aging. In one example, boosting of resistance to premature aging may be due to reducing a person's intrinsic negative response to stress, resulting in increased blood flow to the skin and improved dermal strength, hydration, and tone. In another example, boosting of resistance to premature aging may be due to one or more of the following: reducing serum cortisol, inhibiting enzymes that break down collagen and hyaluronic acid, and/or quenching free radicals with a long-lasting "cascading" antioxidant effect.

An improved health composition of ashwagandha and Indian gooseberry according to the current disclosure may provide advanced skin health rejuvenation. In one example, providing advanced skin health rejuvenation may be influenced by protecting the body from free radical damage after exposure to environmental (extrinsic) aging factors like the sun's rays (UV light) and the toxic chemicals present in cigarette smoke and air pollution. Exposure to the aforementioned factors may result in the formation of unstable, highly reactive, electron-deficient free radical molecules, including reactive oxygen species (ROS) and reactive nitrogen species (RNS). Oxidative stress may occur when these electron-deficient free radicals become stable by stealing electrons from (i.e., oxidizing) neighboring molecules, initiating a chain reaction that destabilizes and destroys important dermal matrix components. An improved health composition of ashwagandha and Indian gooseberry according to the current disclosure may limit free radical damage. In one example, free radical damage may be reduced by preventing free radical formation and/or by displaying free radical quenching antioxidant activity.

An improved health composition of ashwagandha and Indian gooseberry according to the current disclosure may also promote the health and appearance of the skin. In one example, health and appearance of the skin may be promoted by limiting free radical formation and/or by providing anti-oxidative protection of dermal components after free radicals form. Collagen is the predominant protein in the dermal extracellular matrix. When free radicals attack and destroy collagen or change its structure, the skin loses its ability to maintain elasticity and firmness resulting in the formation of lines, wrinkles and sagging skin. Free radicals also attack cellular lipids, DNA, and protein, causing impairment of cell function and eventual cell death.

An improved health composition of ashwagandha and Indian gooseberry according to the current disclosure may present a multi-functional dermal defense system. In one example, a multi-functional dermal defense system may do two or more of the following: (1) lower cortisol and increases DHEA, (2) prevents free radical-induced photoaging, (3) inhibit collagenase activity in vitro, (4) inhibit hyaluronidase activity in vitro, (5) display superior cascading antioxidant activity, (6) reduce C-reactive protein, (7) enhance mood. The following section will describe each of these mechanisms in greater detail.

An improved health composition of ashwagandha and Indian gooseberry according to the current disclosure may promote stress relief and/or a positive mental outlook. Stress not only steals vitality, health and energy, it is one of the primary intrinsic factors of aging. All parts of the body are negatively affected by stress, including the skin. Stress-induced aging results from secretion of the stress hormones cortisol and adrenaline. Cortisol competes with the antiaging hormone dehydroepi-androsterone, also known as DHEA. In stressed individuals, cortisol levels are elevated and DHEA levels are lowered. Additionally, stress hormones such as cortisol and adrenaline cause blood vessels to constrict which reduces vital circulation of blood in dermal tissues. This impedes delivery of oxygen, water, and other vital nutrients to the skin. In one example, the promotion of stress and/or a positive mental outlook may lower serum cortisol levels and increase serum DHEA levels.

An improved health composition of ashwagandha and Indian gooseberry according to the current disclosure may prevent photoaging. In one example, photoaging may be prevented by stopping or slowing several processes that may cause photoaging, the primary extrinsic factor associated with premature aging that occurs when skin is exposed to UV light. Such exposure causes the release of iron ions from the iron-storage protein, ferritin. Unbound iron in the body is dangerous because in the presence of hydrogen peroxide it catalyzes the production of several types of free radicals and reactive oxygen species (ROS) in what is known as the Fenton Reaction. The resulting oxidative stress leads to degradation of collagen and other dermal proteins, producing the lines and wrinkles characteristic of photoaging.

An improved health composition of ashwagandha and Indian gooseberry according to the current disclosure may protect the skin from oxidative photodamage. In one example, protection of the skin from oxidative photodamage may be accomplished through an ability to fully chelate, or bind, iron ions, thereby preventing both catalysis of the Fenton Reaction and subsequent photo-induced free radical formation. This occurs without causing iron deficiency in the body because chelated iron is still bioavailable internally.

Most other antioxidants generally do not chelate iron and are generally actually pro-oxidative under UV conditions (e.g., Vitamin C) because in the presence of iron they accelerate the Fenton Reaction and free radical formation. This seems counterintuitive since it is commonly thought that antioxidants reduce free radical damage because of their ability to donate electrons to oxidizing agents that normally would steal them from biological tissues. This is how antioxidants behave internally or in the absence of UV light, but when the skin is exposed to UV light available electrons in antioxidants are donated to released iron thereby recycling it for use in the Fenton Reaction. It is believed that an improved health composition of ashwagandha and Indian gooseberry according to the current disclosure may not display any significant pro-oxidative properties. In one example, non-display of any significant pro-oxidative properties may be due to the improved health composition's iron chelation property that may eliminate the Fenton Reaction.

Generally, exposure of the skin to UV light results in the production by dermal fibroblast cells of naturally occurring, matrix-degrading metalloproteases (MMPs), which enzymatically break down proteins in the dermal extracellular matrix. MMPs with the most influence on the aging process are collagenases, which break down collagen fibers. Collagen makes up 75-80% of the dermal matrix by weight and is the chief component that adds strength, durability, and elasticity to the skin owing to its high tensile strength and intramolecular bonding that stabilizes the molecule. Collagen molecules that lie closely to one another are also chemically bonded together via covalent cross-linkages, further adding to the strength of the collagen fibrillar meshwork that holds the dermis together. Within hours of exposure to UV light, collagenase activity in the skin increases, disrupting this meshwork by breaking down the collagen molecules that form its infrastructure. Degradation of this kind over an extended period of time leads to loss of skin tone and the fine lines and wrinkles associated with photoaging.

An improved health composition of ashwagandha and Indian gooseberry according to the current disclosure may promote more youthful looking skin. In one example, promotion of more youthful looking skin may be achieved by preventing the breakdown of hyaluronic acid. Hyaluronidase inhibition may be an important contributor to skin health because hyaluronic acid, which is degraded by hyaluronidase, a non-protein component of the skin that is responsible for adding volume and moisture, and giving skin a supple, plump-looking appearance. Hyaluronic acid is located in the amorphous ground substance, which surrounds and cements together collagen fibers in the extracellular space between dermal fibroblasts, and also in the epidermis. Classified as a glycosaminoglycan, hyaluronic acid has chemical properties that attract and bind hundreds of times its weight in water.

An improved health composition of ashwagandha and Indian gooseberry according to the current disclosure may possess a "cascading" antioxidant activity. In one example, cascading antioxidant activity may be achieved through aggressively scavenging free radicals that form in other ways. In another example, cascading antioxidant activity may be achieved through a continuous recycle of antioxidants and therefore may remain active over a longer period of time for increased antioxidant activity. Free radicals form in the body due to intrinsic natural processes such as electron transport associated with mitochondrial activity and immune function.

They are also produced when the body is exposed to such extrinsic factors as chemical pollution or cigarette smoke.

An improved health composition of ashwagandha and Indian gooseberry according to the current disclosure may promote and maintain a healthy response to inflammation. In one example, a promotion and maintenance of a healthy response to inflammation may be due to reducing levels of C-Reative Protein, serum cortisol and/or increasing serum DHEA. C-Reactive Protein is a marker of systemic inflammation in the body that results from cellular injury triggered by environmental or genetic factors. Inflammation can affect skin health and aging through the appearance of redness, flushing, irritation as well as other skin conditions.

An improved health composition of ashwagandha and Indian gooseberry according to the current disclosure may have the ability to enhance mood. In one example, an enhanced mood may be due to increasing resistance to stress, promoting a positive mental outlook, and/or enhancing feelings of well-being. The mind-skin connection is strong. So strong in fact that there is a burgeoning field in dermatology referred to as "psychodermatology" that addresses how an individual's emotional state affects skin health and appearance. Irritability, a negative outlook and other feelings resulting from stress can contribute to aging of the skin through physiological processes similar to how stress affects the rest of the body.

In one exemplary aspect, an exemplary composition as described herein provides improved inhibition of collagenases. In another example, a composition including ashwagandha and Indian gooseberry according to this disclosure provides a synergistic inhibition of collagenases.

In another exemplary aspect, an exemplary composition as described herein provides improved inhibition of hyaluronidase. In another example, an improved health composition including ashwagandha and Indian gooseberry according to this disclosure provides a synergistic inhibition of hyaluronidase.

In yet another exemplary aspect, an exemplary composition as described herein provides improved inhibition of iron chelation. In another example, an improved health composition including ashwagandha and Indian gooseberry according to the disclosure provides a synergistic promotion of iron chelation.

EXPERIMENTAL EXAMPLES

Example 1

An example improved health composition was prepared using:
Ashwagandha
Indian Gooseberry
in a ratio of 5:3 weight to weight (w:w).

An example composition having Indian gooseberry extract without Ashwgandha provided an inhibition of UV-induced collagenase synthesis by 39% in an ex vivo model using human skin fibroblasts. An example improved health composition of ashwagandha and Indian gooseberry was then prepared according to Example 1. This example composition displayed 50% activity inhibition of the primary collagenases in the skin, collagenases Type I and Type IV. FIG. 1 illustrates a plot 100 of relative fluorescence unit (RFU) values over time for three samples. The top plot line 104 represents inhibition data for a control. The middle plot line 108 represents inhibition data for a composition according to Example 1 (4 mg/mL). The bottom plot line 112 represents inhibition data for 0.1 mM 1,10-phenanthroline.

Collagenases, part of a class of matrix-degrading metalloproteases (MMPs), break down collagen fibers. Collagen makes up 75-80% of the dermal matrix by weight and is the chief component that adds strength, durability, and elasticity to the skin owing to its high tensile strength and intramolecular bonding that stabilizes the molecule. Collagen molecules that lie closely to one another are also chemically bonded together via covalent cross-linkages, further adding to the strength of the collagen fibrillar meshwork that holds the dermis together. Within hours of exposure to UV light, collagenase activity in the skin increases, disrupting this meshwork by breaking down the collagen molecules that form its infrastructure. Degradation of this kind over an extended period of time leads to loss of skin tone and the fine lines and wrinkles associated with photoaging. The test results indicate likely synergistic activity of the components of Example 1 in providing high levels of inhibition of collagenase.

Inhibition of Hyaluronidase

| Inhibition Assay | Results |
|---|---|
| Hyaluronidase Inhibition | 86% Inhibition @ 1:1000 |
| | 32% Inhibition @ 1:2000 |
| | No Inhibition @ 1:3000 |
| | No Inhibition @ 1:4000 |

An example improved health composition of ashwagandha and Indian gooseberry was prepared according to Example 1. In an in vitro test regularly used by the cosmetics industry to evaluate skincare products, this composition inhibited hyaluronidase activity by 86% at 1:1000 when compared to a control. This composition provided inhibition of hyaluronidase activity by 32% inhibition at 1:2000.

Hyaluronidase inhibition is an important contributor to skin health. Hyaluronic acid is degraded by hyaluronidase, a non-protein component of the skin that is responsible for adding volume and moisture, and giving skin a supple, plump-looking appearance. Hyaluronic acid is located in the amorphous ground substance, which surrounds and cements together collagen fibers in the extracellular space between dermal fibroblasts, and also in the epidermis. Classified as a glycosaminoglycan, hyaluronic acid has chemical properties that attract and bind hundreds of times its weight in water. The results of this test suggest a potential synergistic activity of the components of Example 1 in inhibition of hyaluronidase.

Iron Chelation Testing

HORAC(μmole CAE/g)154

Example Composition

An example improved health composition of ashwagandha and Indian gooseberry was prepared according to Example 1. This composition displayed a HORAC value of 154 μmole caffeic acid equivalents/g. This value is considerably higher than that published for other antioxidants found in the literature. For example, blueberry extract has a HORAC of 110 units while Vitamin C has a HORAC of 0 units. The unexpectedly high results of iron chelation are likely due to the synergy of the improved health composition of ashwagandha and Indian gooseberry.

For this test, Caffeic acid was used as the calibration standard and the HORAC result is expressed as μmole Caffeic acid equivalent (CAE) per gram. This test evaluates iron chelation by measuring the degree to which a sample inhibits the Fenton Reaction, a condition that catalyzes the production of several types of free radicals and reactive oxygen species (ROS). If no chelation occurs, hydroxyl free radicals are formed, oxidizing a fluorescent compound. If a sample chelates iron, it reduces the Fenton Reaction and free radical formation, which in turn leads to reduced oxidation of the fluorescent compound. Chelation is measured based on the level of fluorescence given off in the presence of the sample compared to a control.

ORAC Testing $ORAC_{hydro}$(μmole TE/g)967

Example Composition

An example improved health composition of ashwagandha and Indian gooseberry was prepared according to Example 1. This composition displayed a $ORAC_{hydro}$ value of 967 μmole TE/g. ORAC is a test of oxygen radical absorbance capacity. A typical ORAC analysis provides a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, is used as the calibration standard the ORAC result is expressed as micromole Trolox equivalent (TE) per gram. The results of the ORAC test show this composition is indicative of cascading antioxidant activity that aggressively scavenges free radicals that form in other ways, thereby protecting delicate skin tissues from aging-related degradation and most other antioxidants lack a recycling capability and lose their function shortly after initiating antioxidant activity. In addition, the high ORAC value of 967 μmole Trolox equivalents/g shows that this compositions recycling capability allows it to maintain its antioxidant activity for an extended amount of time and potentially suggests a synergistic activity of the improved health composition of ashwagandha and Indian gooseberry.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A therapeutic composition for internal use by a human subject in the reduction of premature skin aging consisting essentially of a skin age reducing synergistically effective combination of an extract of *Phyllanthus emblica* and an extract of *Withania somnifera* wherein said *Phyllanthus emblica* and said *Withania somnifera* are present in the composition in a weight ratio of about 1:7 *Phyllanthus emblica* to *Withania somnifera* to a weight ratio of about 7:1 *Phyllanthus emblica* to *Withania somnifera*.

2. The therapeutic composition according to claim 1, wherein said *Phyllanthus emblica* and said *Withania somnifera* are present in the composition in a weight ratio of about 6:2 *Phyllanthus emblica* to *Withania somnifera* to a weight ratio of about 2:6 *Phyllanthus emblica* to *Withania somnifera*.

3. The therapeutic composition according to claim 1, wherein the *Phyllanthus emblica* and *Withania somnifera* are present in the composition in a weight ratio of about 6:2 *Phyllanthus emblica* to *Withania somnifera* to a weight ratio of about 3:5 *Phyllanthus emblica* to *Withania somnifera*.

4. The therapeutic composition according to claim 1, wherein the *Phyllanthus emblica* and *Withania somnifera* are present in the composition in a weight ratio of about 6:2 *Phyllanthus emblica* to *Withania somnifera* to a weight ratio of about 2:2 *Phyllanthus emblica* to *Withania somnifera*.

5. The therapeutic composition according to claim 1, wherein the *Phyllanthus emblica* and *Withania somnifera* are present in the composition in a weight ratio of about 5:3.

6. The therapeutic composition according to claim 1, comprising about 60 wt. % *Withania somnifera* to about 65 wt. % *Withania somnifera* and about 35 wt. % *Phyllanthus emblica* to about 40 wt. % *Phyllanthus emblica*.

7. The therapeutic composition according to claim 1, wherein said synergistically effective combination includes *Phyllanthus emblica* to *Withania somnifera* in a weight to weight ratio that is effective to synergistically inhibit collagenase.

8. The therapeutic composition according to claim 7, wherein said synergistically effective combination includes *Phyllanthus emblica* to *Withania somnifera* in a weight to weight ratio that is effective to provide at least a 50% activity inhibition of collagenases Type I and Type IV.

9. The therapeutic composition according to claim 1, wherein said synergistically effective combination includes *Phyllanthus emblica* to *Withania somnifera* in a weight to weight ratio that is effective to synergistically inhibit hyaluronidase.

10. The therapeutic composition according to claim 9, wherein said synergistically effective combination includes *Phyllanthus emblica* to *Withania somnifera* in a weight to weight ratio that is effective to provide at least 86% inhibition of hyaluronidase activity at 1:1000.

11. The therapeutic composition according to claim 1, wherein said synergistically effective combination includes *Phyllanthus emblica* to *Withania somnifera* in a weight to weight ratio that is effective to provide an ORAC (Oxygen Radical Absorbance Capacity) value of at least 967 μmole Trolox equivalents/g.

12. The therapeutic composition according to claim 1, wherein said synergistically effective combination includes *Phyllanthus emblica* to *Withania somnifera* in a weight to weight ratio that is effective to provide an HORAC (Hydroxyl Radical Antioxidant Capacity) value of 154 μmole caffeic acid equivalents/g.

* * * * *